United States Patent [19]

Angerman et al.

[11] 4,317,240

[45] Mar. 2, 1982

[54] SPORTS GOGGLE

[75] Inventors: Gottfried Angerman, Neuhofen; Otto Armbrust, Traun; Franz Dianitsch, Linz; Berthold Hiebl, Traun, all of Austria

[73] Assignee: Carrera International Corporation, Norwood, N.J.

[21] Appl. No.: 184,794

[22] Filed: Sep. 8, 1980

[30] Foreign Application Priority Data

Dec. 13, 1979 [DE] Fed. Rep. of Germany ....... 2950090
Dec. 20, 1979 [DE] Fed. Rep. of Germany ... 7935863[U]
Jun. 10, 1980 [FI] Finland .................................. 801858

[51] Int. Cl.³ .............................................. A61F 9/02
[52] U.S. Cl. .......................................... 2/436; 2/446; 2/452
[58] Field of Search ................... 2/436, 440, 442, 441, 2/443, 446, 452; 351/44, 41, 62, 87

[56] References Cited

U.S. PATENT DOCUMENTS

| | | | |
|---|---|---|---|
| 2,642,568 | 6/1953 | Stewart | 2/436 |
| 3,015,987 | 1/1962 | Harrison | 2/436 |
| 3,173,147 | 3/1965 | Gross et al. | 2/452 |
| 3,233,250 | 2/1966 | Jonassen | 2/443 |

FOREIGN PATENT DOCUMENTS

| | | | |
|---|---|---|---|
| 1030364 | 3/1953 | France | 2/436 |
| 452519 | 10/1949 | Italy | 2/436 |
| 930735 | 7/1963 | United Kingdom | 2/436 |

*Primary Examiner*—Peter P. Nerbun
*Attorney, Agent, or Firm*—Fitch, Even, Tabin, Flannery & Welsh

[57] ABSTRACT

Sports goggles are formed with anterior and posterior frame sections each having a bow spaced from each other to define a slot to provide increased ventilation of space behind lens and particularly against the rearward surface of the lens for the elimination or reduction of fogging. The anterior frame section carries the lens at a position spaced farther than normal from the wearer's face and posterior frame section carries a nosebridge and temples. These goggles may be economically manufactured by molding lightweight material into a separate anterior frame section and a separate posterior frame section, then joining the two frame sections through tab and slot assembly.

13 Claims, 5 Drawing Figures

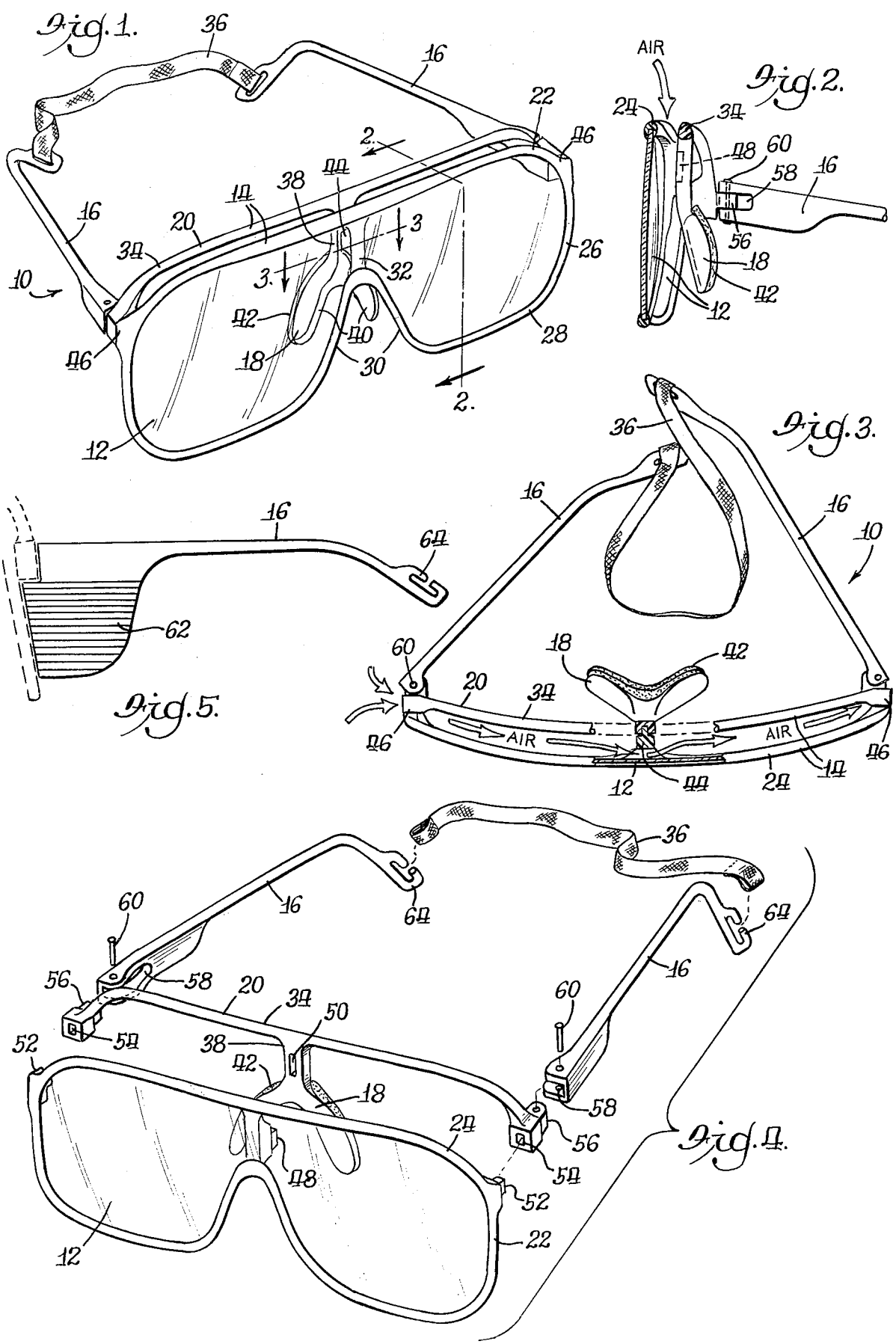

SPORTS GOGGLE

BACKGROUND OF THE INVENTION

The present invention relates generally to a goggle, and more particularly to a sports goggle for use during a sports activity.

Protective goggles are customarily employed for cross-country skiing, bicycle racing and similar types of sports. During sports events, the athlete's body becomes heated and his breath may carry more heat and moisture than a person who is not physically exercising while wearing glasses or goggles. Hence, one problem which attends athletes wearing sport goggles is the formation of fog on the viewing lens or lenses.

Many proposals have been disclosed for avoiding fogging of goggles such as incorporating air flow ventilation passageways in a goggle frame. For example, small adjustable or non-adjustable apertured passageways are formed in the goggle frame to vent the space between the goggle lens and the wearer's face directly to the atmosphere. Apparently, the direction and quantity of air flow against the inner lens surfaces is not sufficient in these goggles to reduce fogging to a level desired for use by cross-country skiers or others who perspire greatly while skiing. For downhill skiing, double lens appear to work well but do not work as well for cross-country skiing.

Anti-fog coatings have been developed. The disadvantage is that the coatings need to be renewed and some tend to interfere with vision as they become contaminated.

Another known method of reducing fog is to deposit thin transparent metallic films on the surfaces of the lenses likely to fog and then pass current through the films to heat the surfaces to keep the surface temperature above the dew point. The disadvantage of this method is the necessity for electrical leads, switch means, and a portable power supply, all to be carried by the wearer. Additionally, this method reduces light transmission and thus may interfere with visibility.

It is suggested in U.S. Pat. No. 3,012,248 to use double—spaced lens with an intervening enclosed air space to impede the transfer of heat from the innermost to the outermost lens surfaces in an attempt to inhibit fogging. The disadvantage is the added weight and cost due to the extra lens elements and the temporary nature of the solution.

In addition to anti-fogging capabilities, sport goggles must be sufficiently lightweight that they are not an undue burben to the wearer and they must be sufficiently strong and tough to withstand abuse. The goggles must also be comfortable to wear and should be fashionable.

SUMMARY OF THE INVENTION

In accordance with the present invention the problems with fogging of the lens in sports goggles have been eliminated or reduced by constructing the goggles with ample space between the lens and the wearer's face to allow air to flow to remove body heat and moisture before they reach the lens. Preferably, the bows and lens are positioned to cause air at the top of the goggle to flow downward against the inner lens surface reducing the heat differential between the front and rear lens surfaces that might cause fogging and removing moisture which might otherwise condense as fog. The preferred embodiment of the invention includes a dual bow design with the lens mounted on an anterior bow section attached in cantilever fashion to a posterior bow section so that ventilation between the wearer's face and the lens is substantially unobstructed. Heat transfer through solid materials is negligible due to the small area joining the anterior and posterior sections.

The dual bow design straightforwardly permits an appropriate distribution of flexibility and rigidity throughout the goggle. The entire goggle may be made of material flexible enough so that the components in contact with the wearer's face may be accommodated comfortably. Strength and toughness is provided by the dual bow construction to avoid disengagement or breakage of the lens.

The dual bow design is susceptible of very economical manufacture. The anterior frame and posterior bow may be molded or otherwise fabricated separately and then joined through tab and slot assembly or other means. Temple bars and/or bands, may be connected in conventional hinged or other manner.

A general object of this invention is to provide a goggle, usable for cross-country skiing and similar sports, which will eliminate or reduce lens fogging.

Another object of this invention is to provide an appropriate distribution of flexibility, toughness and strength.

A still further object is to provide a goggle design susceptible of simple and economic manufacture.

DESCRIPTION OF THE DRAWINGS

FIG. 1 is a perspective view of a preferred embodiment of a sports goggle formed in accordance with the present invention;

FIG. 2 is a partial sectional view taken along line 2—2 of FIG. 1;

FIG. 3 is a top plan view of the sports goggle shown in FIG. 1 with the temples shown in a slightly altered position;

FIG. 4 is an exploded perspective view of the sports goggle shown in FIG. 1;

FIG. 5 is a partial side elevational view illustrating an alternative of form temple which can be used in place of the temple illustrated in FIG. 1.

DESCRIPTION OF THE PREFERRED EMBODIMENT

Referring to the drawings, and in particular to FIG. 1, a goggle 10 constructed in accordance with the preferred embodiment is formed with a lens 12 which preferably is a transparent plastic panel which may be tinted for use under various lighting conditions and may be polarized to provide the desired protection from glare and ultraviolet rays.

The lens 12 is mounted in a frame means 14 and is attached to be held on the wearer's head by attaching means which may be in the form of temples 16 which extend rearwardly from the frame means to the wearer's ears in the conventional manner. The goggles rest on the wearer's nose and are supported by a nose bridge 18.

In accordance with the present invention, the lens 12 is spaced from the wearer's face at a greater distance than is normal and preferably is cantilevered on the frame means 14 in a manner to inhibit fogging of the lens means so that the lens is ventilated to inhibit the transmission of bodily heat and evaporated moisture to the lens 12. This is achieved in the present invention by a dual bow frame means which comprises a posterior frame or bow section 20 carrying the nose bridge 18 and having attachment means for attaching an anterior frame or bow section 22 in which is mounted the lens 12. Preferably the attachment means connects the anterior and posterior frame sections at spaced points which define with the bows an elongated substantially fully opened slot between the respective bows with the lens positioned to cooperate with the bows to define an air foil for deflecting air across the rearward surface of the lens to inhibit or prevent the backup of moisture thereon.

In accordance with the further and important aspect of the invention, the frame means 14 is readily manufactured with the anterior and posterior frame sections being separately molded. The preferred attachment means for joining the anterior and posterior frame sections comprises a mating tab and slot means with tabs 48 and 52 being molded on one of the frame sections and being inserted into the slots 50 and 54 molded into the other frame section with a suitable adhesive or securing means being applied to hold the tabs in slots against separation therefrom. Herein, the tabs are formed at the center and the ends of the anterior frame section for insertion into similarly located slots formed in the posterior frame section.

Referring now in greater detail to the preferred embodiment of the invention, the anterior frame section 22 comprises a one piece molded frame which encircles and supports the lens 12. Along the top of the anterior frame section is an anterior bow 24 in the form of a generally horizontally extending bar or thin segment which lead to side lens supporting segments 26 which extend downwardly from the bow along the vertical sides of the lens. The side lens supporting segments lead to lower lens supporting segments 28 which are joined by a nose receiving indentation or groove 30 formed in the underside of the anterior frame section 22 to accomodate the wearer's nose. An inwardly facing groove (not shown) is formed into the inner periphery of the anterior frame section for receiving in a snap fit relation the conforming edge of the flexible lens 12. A suitable adhesive may be used to secure the lens in the groove and against removal from the groove. A center segment 32, rearward from the lens, leads from the center of the anterior bow 24 downwardly to the crest of the nose indentation or groove 30.

A posterior bow 34 of the posterior frame section 20 parallels the anterior bow 24; the parallel bows 24 and 34 are spaced approximately six millimeters apart. The nose bridge 18 in the form of an inverted "Y" leads downward from the center of the posterior bow.

Preferably, the posterior frame section 20 is also molded in a single piece of similar material to that used for the anterior frame section and is provided with a posterior bow 34 which is spaced from and closely parallel to the anterior bow once the frame sections are assembled. From the center of the posterior bow depends a nose bridge 18 which includes an upper vertical bar segment 38 and a lower integral forked portion 40 resting on the nose. A soft nose pad 42 such as of plastic foam is glued to the downwardly facing sides of the forked portion for resting on the wearer's nose.

The attachment means for joining the anterior and posterior frame sections comprises a center bridge projection 44 and two lateral bridge projections 46 which define the only areas of contact between the anterior frame section 22 and the posterior frame section 20. The three bridge projections serve to connect and space the frame sections. The bridge projections are the results of tab and slot assembly (FIG. 7). A center tab 48 which is a molded part of the anterior frame section and located on the rear side of the center segment 32. When the center tab is glued and inserted into a center slot 50 molded into the vertical bar segment 38 of the posterior frame section 20, it defines the center bridge projection. Two lateral tabs 52 are also molded into integral portions of the anterior frame section and are located at the rear of the lateral extremities of the anterior bow 24. When glued and inserted into two forward facing lateral slots 54 molded into the lateral extremities of the posterior bow 34, the lateral tabs define the lateral bridge projections 46.

Integrally molded on the posterior frame section 20 are hinge nubs 56 located at the rearward facing side of the lateral extremities of the posterior bow 34 for receiving a hinged attachment with the temples 16. More specifically, hinge forks 58 are molded into the temples to receive therebetween a hinge nub. Hinge pins 60 are inserted through the forks and nubs to hinge. This assembly permits rotation of the temples from a rearward position to a folded position, as is conventional for many glasses and goggles. The temples may have flanges 62 (FIG. 5) to provide additional protection from wind, airborne particles and glare. As shown in FIGS. 4 and 5, the temples 16 are provided with "C" mounts 64 for the attachment of a headband 36.

The anterior frame section 22, the posterior frame section 20, and the two temples 16 may be molded separately out of a suitable, conventional epoxy resin material. The molding may, for example, be in accordance with the process described in Hampel U.S. Pat. No. 3,708,567. The resultant goggle exhibits the following desirable qualities: high impact strength, shock absorption, excellent shape retention, and low water (sweat) absorption. The epoxy material used in the process is lightweight and economical to cast, and thus the goggle 10 itself exhibits these properties.

The flexibility and the flexural strength of the epoxy material used is such that in the one to six millimeter thicknesses used throughout the goggle comfortably accommodates the wearer while maintaining the basic goggle shape. In particular, the temples 16 will conform in use to the line of the wearer's head, and the nose bridge 18, being cantilevered from the center bridge projection 44 and being of lesser thickness, approximately two millimeters, conforms readily to the extension and shape of the wearer's nose. The foam rubber nose pad 42 glued to the nose bridge further adds to wearer comfort.

The posterior bow 34 is attached and positioned relative to the anterior bow 24 in such a way that the natural flexing of the anterior bow is opposed. Thus the frame provides the extra rigidity necessary for lens support in the anterior frame section 22 otherwise made of relatively flexible material.

Among the more important properties of the dual bow design are aerodynamics to inhibit fogging. As a result of the design there is a greater distance between the face of the wearer and the lens 12 than there would normally be in a single frame design. The additional distance impedes the transfer of body heat and moisture from the wearer's face to the lens that might otherwise cause fogging. The fact that the lens and anterior frame section are connected to the body contact points of the goggle only through the three bridge projections minimizes the conduction of heat through solid channels.

The skeletal form of the posterior frame section 20 and the temples 16 provides room for a substantial air flow between the lens and the wearer's face, especially under the usual moving conditions of sports such as cross-country skiing and bicycle racing. In the variation of FIG. 5 with the temple flanges 62 the air flow remains substantial, though somewhat diminished. The abundant ventilation helps remove body heat and moisture from the space between the wearer's face and the lens so that they are less able to contribute to fogging.

It is thought that the posterior bow 34 aids in deflecting air into the interstice between the anterior 24 and the posterior 34 bows and against the rearward surface of the lens. The downward incline of the lens is rearward so as to maintain the downward airflow against the inner surface of the lens. Thus, fresh air is forced against the rearward surface of the lens thereby inhibiting or preventing moisture buildup at the rearward surface.

In the dual frame design, the position and the shape of the nose bridge 18 reinforce the deflected airflow against the inner surface of the lens 12. Much of the air impinging on the nose area of the wearer will be deflected laterally against the lens in both lateral directions from the center. The lateral incline of the lens is rearward, again enhancing the effect of the deflected airflow on the rearward surface of the lens. Thus the dual frame design uniquely directs abundant ventilation to the areas where it will be most efficacious in preventing fogging.

While the above is the preferred embodiment of the invention, the invention is susceptible of embodiment in many different forms, examples of which follow. As pointed out above, the temples may be flanged or unflanged; the temple segments may be replaced by a headband. The lens may be rigid or flexible, polarized or not, two piece or one piece, and tinted or not. The goggle may be made of a variety of materials, including epoxies, plastics and metals. The anterior frame may only partially enclose the lens. It should be understood from the possible variations that the above disclosure is to be considered as an exemplification of the principles of the invention and is not intended to limit the invention to the embodiment illustrated.

What is claimed is:

1. A goggle comprising:
   a single lens means;
   an anterior frame section having a bow and extending across at least the upper portion of said lens means and supporting the single lens means;
   a posterior frame section for supporting said anterior frame section and having a bow extending generally parallel to said bow of said anterior frame and for positioning adjacent the brow of the wearer and defining a slot with said bow on said anterior frame section for the flow of air to said lens means;
   a nose piece on said posterior frame section for resting on the wearer's nose;
   spacer means connecting said anterior and posterior frame sections and spacing the same with the slot between said bows; and
   means connected with the end of said posterior frame section for connection to wearer's head for maintaining the position of the goggle on the wearer's face.

2. A goggle in accordance with claim 1 wherein the spacer means connecting the anterior and posterior frame sections consist of bridge projections at three points on each frame section leaving a substantially unobstructed slot and an open space between said frame sections for ventilation between the frames.

3. A goggle comprising:
   a viewing means;
   an anterior frame section framing and supporting said viewing means;
   a posterior frame section, including a posterior bow and a nose bridge;
   bridge projections molded integrally with said frame sections spacing and connecting said frame sections, one bridge projection in the center area of the goggles, and one bridge projection at each of the lateral extremities of the goggles, said bridge projections defining an open interstice between said frame sections providing substantial unobstructed ventilation between said frame sections, said bridge projections providing limited surface area for the transfer of body heat to said viewing means, said bridge projections spacing said viewing means forwardly of said posterior frame section to limit the transfer of body heat and moisture to the rearward surfaces of said viewing means thereby reducing fogging; and
   means connected with the end of said posterior frame section for connection to the wearer's head for maintaining the position of the goggle on the wearer's face.

4. A goggle in accordance with claim 1 or claim 3 wherein the viewing means is a single transparent panel which is colored or polarized to provide protection from glare.

5. A goggle in accordance with claim 1 or claim 3 wherein the viewing means comprises two or more transparent panels or lens elements.

6. A goggle in accordance with claim 1 or claim 3 wherein the means for connecting said frame sections to the wearer's head comprises hinge nubs molded into the rearward portion of the extremities of the posterior bow, temples having hinge forks, hinge pins for joining the hinge nubs to said hinge forks and for forming hinges which permit the temples to pivot between an open position for use and a folded position for storage.

7. A goggle in accordance with claim 3 wherein said nose bridge includes a nose bar connected to the posterior bow in a cantilevered manner for flexibility and is flanged laterally to direct air currents against the rearward surface of the viewing means to reduce fogging.

8. A goggle comprising:
   a transparent panel;
   an anterior frame section for framing and supporting said transparent panel, said anterior frame section being molded of one piece and having an integral lens supporting portion including a bow, said anterior frame section having an integral central tab and integral lateral tabs projecting rearwardly from the anterior bow;
   a posterior frame section for mounting on the wearer's face and for supporting said anterior frame section, a bow on said posterior frame section which parallels the anterior bow, the anterior bow and posterior bow defining an interstice through which air passes against the rear surface of said transparent panel, a nose bridge means extending downwardly from the center of the posterior bow for engaging the wearer's nose, forwardly facing slots molded into the posterior bow for receiving the tabs of said anterior frame section, said tabs serving as bridge projections spacing and connecting said anterior and posterior frame sections; and a pair of temples hingedly mounted on said posterior frame section for extending to the wearer's ears.

9. A goggle in accordance with claim 8 wherein the temples have downwardly extending flanges at their forward extremities to help protect the wearer's eyes against wind, airborne particles and glare at the lateral peripheries of vision.

10. A goggle in accordance with claim 8 wherein said temples have "C" slots on their rear extremities, said "C" slots having an oblique gap of approximately three millimeters which is large enough for the insertion of the headband, but small enough to prohibit disengagement during normal use.

11. A goggle in accordance with claim 3 or claim 8 in which a foam rubber pad is glued to the rearward surface of the nose bridge means for additional wearer comfort.

12. A goggle in accordance with claim 8 wherein the anterior frame section and the posterior frame section are molded separately of duroplastic or epoxy materials.

13. A goggle in accordance with claim 12 in which the temples are molded separately of duroplastic or epoxy materials.

* * * * *